United States Patent
Jones et al.

(10) Patent No.: US 10,525,205 B2
(45) Date of Patent: Jan. 7, 2020

(54) DISPENSE MECHANISM FOR A DRUG DELIVERY DEVICE AND DRUG DELIVERY DEVICE

(71) Applicant: Sanofi-Aventis Deutschland GmbH, Frankfurt am Main (DE)

(72) Inventors: Matthew Jones, Warwickshire (GB); Samuel Steel, Warwickshire (GB); Neal Alexander Blundred, West Midlands (GB); Joseph Butler, Warwickshire (GB); Robert Veasey, Warwickshire (GB); David Aubrey Plumptre, Worcestershire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 276 days.

(21) Appl. No.: 15/313,900

(22) PCT Filed: May 27, 2015

(86) PCT No.: PCT/EP2015/061634
§ 371 (c)(1),
(2) Date: Nov. 23, 2016

(87) PCT Pub. No.: WO2015/181197
PCT Pub. Date: Dec. 3, 2015

(65) Prior Publication Data
US 2017/0224925 A1     Aug. 10, 2017

(30) Foreign Application Priority Data
May 28, 2014 (EP) .................................. 14170379

(51) Int. Cl.
*A61M 5/315* (2006.01)
*A61M 5/19* (2006.01)
(Continued)

(52) U.S. Cl.
CPC .......... *A61M 5/31553* (2013.01); *A61M 5/19* (2013.01); *A61M 5/2033* (2013.01);
(Continued)

(58) Field of Classification Search
CPC .. A61M 2005/2026; A61M 2005/3126; A61M 2205/581; A61M 5/19; A61M 5/20;
(Continued)

(56) References Cited

U.S. PATENT DOCUMENTS

2013/0231613 A1* 9/2013 Leak .................. A61M 5/19 604/191

FOREIGN PATENT DOCUMENTS

| GB | 2497375 | 6/2013 | |
|---|---|---|---|
| WO | WO 2012/072533 | 6/2012 | |
| WO | WO-2012072533 A1 * | 6/2012 | ............. A61M 5/19 |

OTHER PUBLICATIONS

International Preliminary Report in International Application No. PCT/EP2015/061634, dated Nov. 29, 2016, 8 pages.
(Continued)

*Primary Examiner* — Brandy S Lee
(74) *Attorney, Agent, or Firm* — Fish & Richardson P.C.

(57) ABSTRACT

A dispense mechanism for a drug delivery device for the delivery of a primary medicament in a primary cartridge and a secondary medicament in a secondary cartridge includes a primary drive member and a secondary drive member serve for driving a primary and a secondary lead screw. The primary drive member and the secondary drive member are configured to rotate during dose dispense. A coupling member serves for rotationally coupling the primary drive member to the secondary drive member and moves from a first position in which the primary drive member is rotationally decoupled from the secondary drive member into a second position in which the primary drive member is rotationally
(Continued)

coupled to the secondary drive member during dose dispense. Rotation of the primary drive member moves the coupling member from the first position into the second position.

18 Claims, 5 Drawing Sheets

(51) Int. Cl.
    *A61M 5/20*     (2006.01)
    *A61M 5/32*     (2006.01)
    *A61M 5/31*     (2006.01)

(52) U.S. Cl.
    CPC ...... *A61M 5/31541* (2013.01); *A61M 5/3295* (2013.01); *A61M 2005/2026* (2013.01); *A61M 2005/3126* (2013.01); *A61M 2205/581* (2013.01)

(58) Field of Classification Search
    CPC ............ A61M 5/2033; A61M 5/31541; A61M 5/31553; A61M 5/3156; A61M 5/31561; A61M 5/31583; A61M 5/3295; A61M 2025/0019; A61M 25/00; A61M 25/0108; A61N 2005/0629; A61N 2005/063; A61N 2005/0651; A61N 2005/0654; A61N 2005/0656; A61N 2005/0659; A61N 2005/0663; A61N 2005/067; A61N 5/0601; A61N 5/062; A61N 5/0624
    See application file for complete search history.

(56) References Cited

OTHER PUBLICATIONS

International Search Report and Written Opinion in in International Application No. PCT/EP2015/061634, dated Sep. 8, 2015, 10 pages.

* cited by examiner

DISPENSE MECHANISM FOR A DRUG DELIVERY DEVICE AND DRUG DELIVERY DEVICE

CROSS-REFERENCE TO RELATED APPLICATIONS

This application is a National Stage application under 35 U.S.C. § 371 of International Application No. PCT/EP2015/061634, filed May 27, 2015, which claims the benefit of EP Application No. 14170379.3, filed on May 28, 2014. The disclosures of the prior applications are incorporated by reference in their entirety.

TECHNICAL FIELD

The present disclosure is directed to a dispense mechanism for a drug delivery device for the delivery of a primary medicament contained in a primary cartridge and a secondary medicament contained in a secondary cartridge.

BACKGROUND

Certain disease states require treatment using one or more different medicaments. Some drug compounds need to be delivered in a specific relationship with each other in order to deliver the optimum therapeutic dose. Here, combination therapy may be desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus. Another example of a medicament combination is the administration of a pain reliever in combination with a medicament for treating osteoarthritis.

Drug delivery devices of the aforementioned kind often have applications where regular injection by persons without formal medical training occurs. This is increasingly common among patients having diabetes or the like, e.g. osteoarthritis. Self-treatment enables such patients to conduct effective management of their disease. In combination therapy, a primary medicament and a secondary medicament are delivered in a specific relationship to deliver the optimum therapeutic dose.

In some cases, depending on the patient or the stage of the therapy, an effective treatment requires variations in the quantities and/or proportions of the medicaments making up the combined therapy. For example, the patient may require a non-adjustable fixed dose of the secondary medicament in combination with an adjustable variable dose of the primary medicament.

The effectiveness of a combined delivery of medicaments may require one or more doses to be delivered sequentially with one of the two medicaments being injected into the human body prior to the delivery of the other medicament. Such treatment may be conducted with devices that include two separate dispensing mechanisms in one injection or drug delivery device that are actuated independently from each other such that the dispensing mechanisms are activated successively. The primary medicament, e.g. a long-acting insulin, is stored in a primary cartridge, while the secondary medicament, e.g. GLP-1 is stored in a separate secondary cartridge. The device comprises two separate dispense rods, such as lead screws, piston rods or the like. The dispense rods have a distal end respectively, which is usually equipped with a bearing or the like to move a bung in the respective cartridge towards a dispensing end such that the respective content of the cartridge is dispensed. For the injection, both cartridges may be connected to a common needle hub with a single injection needle. Some kinds of drug delivery assemblies comprise a compartment such as one or more cartridge holders for respectively accommodating a replaceable medicament container such as a cartridge which stores the respective medicament.

The separate actuation of the dispense mechanisms is often expensive. The user is required to set and dispense the required dose of the primary medicament with the first dispense mechanism and to set and dispense the required dose of the secondary medicament with the second dispense mechanism. Sometimes patients require merely a dose of one of the medicaments, e.g. the primary medicament without a dose of the secondary medicament. Overall, the correct use of the device may be hazardous for patients that are physically or mentally impaired or otherwise disadvantaged. Patients may forget to set the device for injection of one of the medicaments, which includes a significant risk to the user. There is also the risk of operating errors. For example, the user may set a wrong dose of the secondary medicament, which may have a negative effect on the treatment. As effective therapy treatment may also require a strict order in the dispense sequence, in which one the medicaments is dispensed prior to the other of the medicaments, the operation of the device may be challenging, as well.

SUMMARY

Certain aspects of the present invention can improve the dispense capabilities of a drug delivery device of the aforementioned kind and provide a high degree of user convenience in terms of use and safety.

In certain aspects, a dispense mechanism includes a primary drive member for driving a primary lead screw, preferably in a distal direction, and a secondary drive member for driving a secondary lead screw, preferably in a distal direction during dose dispense. The respective movement to drive the lead screw in distal direction may be referred to as the driving movement of the respective drive member. The primary drive member and the secondary drive member are configured to rotate during dose dispense. A coupling member is configured for rotationally coupling the primary drive member to the secondary drive member and configured to move during dose dispense from a first position, in which the primary drive member is rotationally decoupled from the secondary drive member, into a second position, in which the primary drive member is rotationally coupled to the secondary drive member. The coupling member is coupled to the primary drive member during dose dispense such that rotation of the primary drive member moves the coupling member from the first position into the second position. As a result, rotation of the primary drive member is transferred to the secondary drive member, when the secondary drive member is in the second position. Consequently, the dispense of the secondary medicament starts automatically.

The proposed mechanism effectively enables the user to inject the medicaments in a strict order with the primary medicament being dispensed prior to the secondary medicament as the actuation of the secondary drive member depends on the actuation of the primary drive member and the subsequent travel of the coupling member from the first position into the second position. Further, extra setting actions for setting a dose of the secondary medicament are not required as the coupling of the primary drive member and the secondary drive member automatically transfers a dispensing force to the secondary drive member when the coupling member is moved from the first position into the second position during the dispense of the primary medicament. While the user is able to inject a variable dose of the primary medicament, a fixed dose of the secondary medicament can automatically be injected so that the user received the optimal treatment of this disease.

In particular, the primary drive member and the primary lead screw constitute components of a variable dose mechanism, while the secondary drive member and the secondary lead screw constitute components of a fixed dose mechanism. The term "fixed dose" as used herein can be characterized as a dose value that is defined by the construction of the drug delivery device, wherein the user is only able to inject a specific dose. The user is not in the position to set lower or higher doses of medicament and/or to inject lower or higher doses of the medicament. The dose the user may effectively set and inject is restricted to a certain value.

On the contrary, the term "variable dose" can be characterized as a dose where the user is substantially free to choose the amount of medicament he wants to inject. The dose is variably adjustable, normally between upper and lower limits.

Preferably, the coupling member couples the primary drive member to the secondary drive member after a majority of the primary medicament is dispensed and/or when the amount of the secondary medicament of a set dose that has not yet been dispensed during the dispense process has reached a predetermined value. In other words, the dispense of the secondary medicament is initiated, when the remainder of a set dose of the primary medicament during injection reaches a certain threshold value. For that purpose, the coupling member may be movable in axial direction between a maximum distal position and a proximal position which may depend on the dialed dose, wherein when the coupling member moves in distal direction during dose dispense, at a predetermined distance from the maximum distal position, e.g. an end stop or a zero dose unit position, the coupling member engages the secondary dose member and rotation from the primary drive is transferred to the secondary drive member over the remaining distance. A reliable fixed dose mechanism can easily be obtained thereby.

In particular, the proposed dispense mechanism is designed for drug delivery devices with a housing or a housing assembly that extends from a proximal end to a distal end along a longitudinal axis and that accommodates the primary and the secondary drive member and the coupling member. The primary lead screw and the secondary lead screw may be arranged in a parallel relationship to each other and may be parallel offset to the longitudinal axis of the drug delivery device housing. The primary drive member and the secondary drive members may be rotatable around a longitudinal axis, respectively, wherein the respective axis of rotation is concentric to the axis of the respective lead screw. Both drive members may remain stationary in axial direction during the dispense process, e.g. the primary and secondary drive member may be axially constrained in the housing assembly. The primary and the secondary drive member engage the respective lead screw in such way that rotation of the respective drive member causes the respective lead screw to displace in distal direction such as to displace a bung in a cartridge and dispense the respective medicament. Preferably, the coupling member is moveable along the longitudinal axis of the primary lead screw relative to the housing assembly.

The distal end of the drug delivery device is usually referred to as the dispensing end where the drug delivery device may be equipped with a single dispense interface, such as a needle hub with an injection needle. The proximal end is opposite the distal end may be referred to as the setting end where a user operates a dose dial grip or the like to set medicament doses.

The primary medicament, e.g. a long-acting insulin, may be contained in primary reservoir or cartridge that is coupled to the distal end of the drug delivery device so that the primary lead screw moves in distal direction during dose dispense and urges a bung in the primary reservoir distally such that the primary medicament is dispensed. The secondary medicament, e.g. GLP-1, may be contained in a secondary reservoir or cartridge that is coupled to the distal end of the drug delivery device or accommodated in the distal end of the drug delivery device so that the secondary lead screw moves in distal direction during dose dispense and urges a bung in the secondary reservoir distally such that the secondary medicament is dispensed. Accordingly, two cartridges can be coupled to or housed in the drug delivery device.

According to a further embodiment, the coupling member is rotationally coupled to the primary drive member during dose dispense. For example, the coupling member may be coupled to the primary drive member via a dial grip, wherein the coupling member is rotationally keyed to the dial grip.

The primary drive member and/or the secondary drive member may be configured as a drive sleeve, respectively, which at least partly surround the respective lead screw.

Preferably, the coupling member is moveable between said first and said second position relative to the primary drive member and/or the secondary drive member, preferably in axial direction. The first position may correspond to a proximal position, while the second position may correspond to a distal position. While in the proximal position, the driving movement of the primary drive member is not transferred to the secondary drive member, wherein when the coupling member is in the second position, driving movement of the primary drive member is transferred to the secondary drive member and the secondary lead screw moves in distal direction.

Preferably, the coupling member is threaded to the housing assembly or a housing component such that during dose dispense, the coupling member moves in axial direction relative to the housing assembly in a helical movement and into engagement with the secondary drive member. Accordingly, the coupling member may be configured to move in a helical movement with respect to a rotational axis of the primary drive member. Preferably, engagement between the coupling member and the secondary drive member takes place when a predetermined dose of the primary medicament is left to be dispensed. Then the coupling member engages the secondary drive member and rotationally couples the primary drive member to the secondary drive member until the coupling member reaches the end position and the disposing process is finished.

For efficiently transferring rotational movement and torque, a further embodiment provides that the secondary drive member and the coupling member are configured for meshed engagement. The secondary drive member and the coupling member may comprise gear tooth features such that rotation of the primary drive member in one direction causes the secondary drive member to rotate in an opposite direction. For example the coupling member may comprise a first gear element and the secondary drive member may comprise a second gear element configured for meshed engagement with the first gear element when the coupling member is brought into engagement with the secondary drive member by rotation of the primary drive member. Accordingly, the coupling member may be movable in axial direction relative to the primary drive member and/or the secondary drive member between a first axial, e.g. proximal position, in which the gear elements are not engaged in a distal position, in which the gear elements are engaged. Different gear ratios may be provided. Thereby, a precise displacement of the secondary lead screw can be achieved.

According to a further embodiment, a power reservoir for rotating the primary drive member is provided. The power reservoir may comprise a spring, which may be a preloaded (pre-charged) spring or a spring which has to be loaded by the user during dose setting. Preferably, the spring is factory pre-charged for the expected life of the device, i.e. such that a user is not required to re-charge or strain the spring at any time. Suitable spring types involve compression springs and/or torsion springs. Such a spring may include a factory charged tensator spring or the like. The spring may be a reverse wound flat spiral spring, which is a wound up band-type spring which is wound up in its charged state counter to its unstressed winding direction. A first end of the spring may be attached to the housing element and a second end may be attached to the primary drive member. Drug delivery devices of this specific kind are known as auto-injectors.

Sequential delivery of the primary and the secondary medicament can be improved by configuring the secondary lead screw such that when the secondary drive member is rotated, the secondary lead screw advances in distal direction relative to the secondary drive member in a first phase of the rotation of the secondary drive member during dose dispense and such that the secondary lead screw remains stationary in axial direction with respect to the rotating secondary drive member in a subsequent second phase of the rotation of the secondary drive member. In other words, when the secondary drive member starts to rotate under the force of the primary drive member, the secondary lead screw moves in distal direction. After a predetermined axial displacement of the secondary lead screw, rotation of the secondary drive member does not cause axial displacement of the secondary lead screw. In particular, this mechanism ensures that an injection needle or a needle hub is always flushed with the primary medicament at the end of each injection, thereby making sure that the entire secondary medicament is dispensed. A high degree of user safety is obtained. Further, a very precise sequence control can be achieved, wherein a variable dose of the primary medicament is dispensed until the secondary drive member is rotationally coupled to the primary drive member, wherein the secondary medicament is then dispensed until the secondary lead screw stops moving in distal direction and wherein only the primary medicament is dispensed in a final dose when the secondary lead screw stops moving in distal direction.

For efficiently disabling the distal displacement of the secondary lead screw while rotation of the primary drive member is transferred to the secondary drive member, a further embodiment provides that the secondary lead screw comprises a thread, wherein said thread comprises helical segments and non-helical segments.

Preferably, the secondary lead screw is rotationally keyed to the secondary drive member such that the secondary lead screw is rotationally fixed to the secondary member but can displace axially relative to the secondary drive member. Further, the secondary lead screw may be in threaded engagement with the housing assembly, said thread engagement comprising said helical segments and non-helical segments. For example, said segments may be formed on an outer surface of the secondary lead screw. Conceptually, it is also possible that the secondary lead screw is in threaded engagement with the secondary drive member with said helical segments and non-helical segments, while being splined to the housing assembly.

According to a further embodiment, the dispense mechanism comprises a user actuateable dial grip and a lock mechanism, wherein the lock mechanism is configured to rotationally lock the dial grip to the primary drive member during dose dispense. The user may interrupt the dispense sequence and has full control of his injection. The dial grip may extend though an outer surface of the housing assembly and may comprise a clicker arm or the like for engaging at least one corresponding tooth on the primary drive member. The lock mechanism may comprise a trigger lock movable in axial direction with respect to the primary drive member and the dial grip between a proximal position and a distal position. The trigger lock may urge the clicker arm of the dial grip into engagement with the primary drive member, e.g. in radial inward direction, when the trigger lock is moved in axial direction, preferably from a distal position into a proximal position such that the primary drive member is rotationally locked to the dial grip. A user actuateable release mechanism such as a trigger or the like may be configured to move the trigger lock in axial direction when actuated or moved by the user. The trigger lock may be axially splined in the housing assembly, e.g. by a groove-nut engagement or a splined connection.

Efficient control of the dispense sequence is achieved by a lock element configured to prevent the primary drive member from driving the primary lead screw prior to dispense. Said lock element may engage the primary drive member such that the primary drive member cannot rotate under the force of the power reservoir. The trigger may be configured to disengage the lock element from the primary drive member when actuated such that the primary drive member is free to rotate around the longitudinal axis of the primary lead screw. The lock element may be formed on or attached to the above described trigger lock and may comprise teeth features for engaging corresponding teeth features on the primary drive member, wherein actuation of the trigger causes the trigger to move the lock element, respectively the trigger lock, such that the trigger lock disengages from the primary drive member, e.g. by moving the trigger lock in proximal direction from a distal position in which the trigger lock engages and rotationally locks the primary drive member, such that the primary drive member becomes free to rotate under the force of the power reservoir. Engagement of the teeth features rotationally locks the primary drive member.

Preferably, the coupling member is movable relative to the primary drive member comprises a stop feature for locking the primary drive member against rotation after a set dose of the primary medicament is dispensed. For that purpose, a stop feature, e.g. a projection or the like on the coupling member may engage a stop feature, e.g. a projection or the like, on the housing assembly when the set dose of the primary medicament is dispensed such that the coupling member and the primary drive member are prevented from rotating. Efficient control is the dispense mechanism can be achieved thereby, in particular when a pre-charged power reservoir is used.

Very precise dispense control can be achieved when the coupling member is rigidly connected to a dose dial component, wherein the dose-dial component may be a sleeve-like element which is in threaded engagement with the housing assembly so that the dose dial component moves axially with respect to the housing and the primary drive member in a helical movement during dose setting and dose dispense. Preferably, the dose dial component is configured to move in proximal direction during dose setting and in distal direction during dose dispense.

The dose dial component may be moveable between a proximal position and a distal position, wherein the most extreme distal position corresponds to a set dose of the zero units, respectively the end position of the dispensing process and wherein the movement of the dose dial component in proximal position corresponds to an increasing set dose of the primary medicament.

The dose dial component may be a number sleeve or a dose indicator sleeve, preferably provided with numbers or the like to indicate the set dose of the primary medicament. By directly forming the stop feature on the dose dial component, it is efficiently ensured that only the set dose of the primary medicament is dispensed.

According to a further embodiment, a biasing member such as a spring arm on the trigger lock is configured to urge the secondary drive member in a rotational direction opposite a driving direction. The driving direction is the direction, the secondary drive member rotates during dose dispense. This mechanism ensures the accurate dispense of the fixed dose dispense when a dose greater than a prime dose is dialed.

The coupling member may be configured to move from the second position in a direction towards the first position during dose setting such that the rotational coupling between the primary drive member and the secondary drive member is removed. Preferably, the primary drive member is decoupled from the secondary drive member when a pre-determined dose of the primary medicament is set by rotating the dose dial component which moves in proximal direction during dose setting. During the setting process, rotation of the secondary drive member may cause movement of the secondary lead screw. The biasing member guarantees that the secondary drive member is reset into the position prior to dose setting for the later dispense. For example, the secondary drive member may comprise ratchet features, engaged by the spring arm of the biasing member.

According to a further embodiment, the biasing member is configured to disengage from the secondary drive member during dispense. Effective resetting of the secondary drive member and precise disengagement of the biasing member from the secondary drive member is ensured when the biasing member is operably coupled to the lock mechanism, in particular the trigger lock. In particular, the biasing member may be coupled or axially constrained to the trigger lock such that displacement of the trigger lock in axial, in particular proximal direction causes the biasing member to disengage from the secondary drive member. For that purpose, the trigger lock may be formed with said spring arm for engaging said ratchet features formed on the secondary drive member, wherein the spring arm is prestressed when the coupling member rotates the secondary drive member during dose setting until the coupling member disengages from the secondary drive member such that when the coupling member disengages from the secondary drive member, the secondary drive member is reset by the biasing member.

As indicated above, the housing may include a housing assembly, which may be adapted to be connected to or to receive two single medicament cartridges. The housing assembly may comprise two sub-assemblies configured for mutual attachment, one comprising the primary drive member and the primary lead screw and the other comprising the secondary drive member and the secondary lead screw. When a cartridge is empty, the relevant sub-assembly may be discarded and replaced. Preferably, the two sub-assemblies engage between the secondary drive member and the coupling member and the lock mechanism so that the sub-assemblies can easily be separated.

In certain aspects, a drug delivery device is configured for the delivery of two medicaments from separate cartridges. The drug delivery device includes a dose dispense mechanism as described herein.

The drug delivery device can be a disposable injection device. Such devices can be thrown away or recycled after the content of the medicaments has been exhausted. Certain aspects of the present invention are also applicable with re-usable devices designed to replace an empty cartridge with a filled one after the whole content of the former cartridge has been administered. Alternatively, the single sub-assembly may be configured disposable.

In certain aspects, the devices may be used for the combined delivery of a range of medicaments, especially fluid medicaments from two separate cartridges.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antihousing or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-539),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2,
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antihousing is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antihousing; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by A and K. A light chain has two successive domains: one constant domain (CL) and one variable domain (VL). The approximate length of a light chain is 211 to 217 amino acids. Each antihousing contains two light chains that are always identical; only one type of light chain, κ or λ, is present per antihousing in mammals.

Although the general structure of all antibodies is very similar, the unique property of a given antihousing is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antihousing fragment" contains at least one antigen binding fragment as defined above, and exhibits essentially the same function and specificity as the complete antihousing of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

An exemplary embodiment will now be described with reference to the accompanying drawings in which.

DETAILED DESCRIPTION

Figure 1:
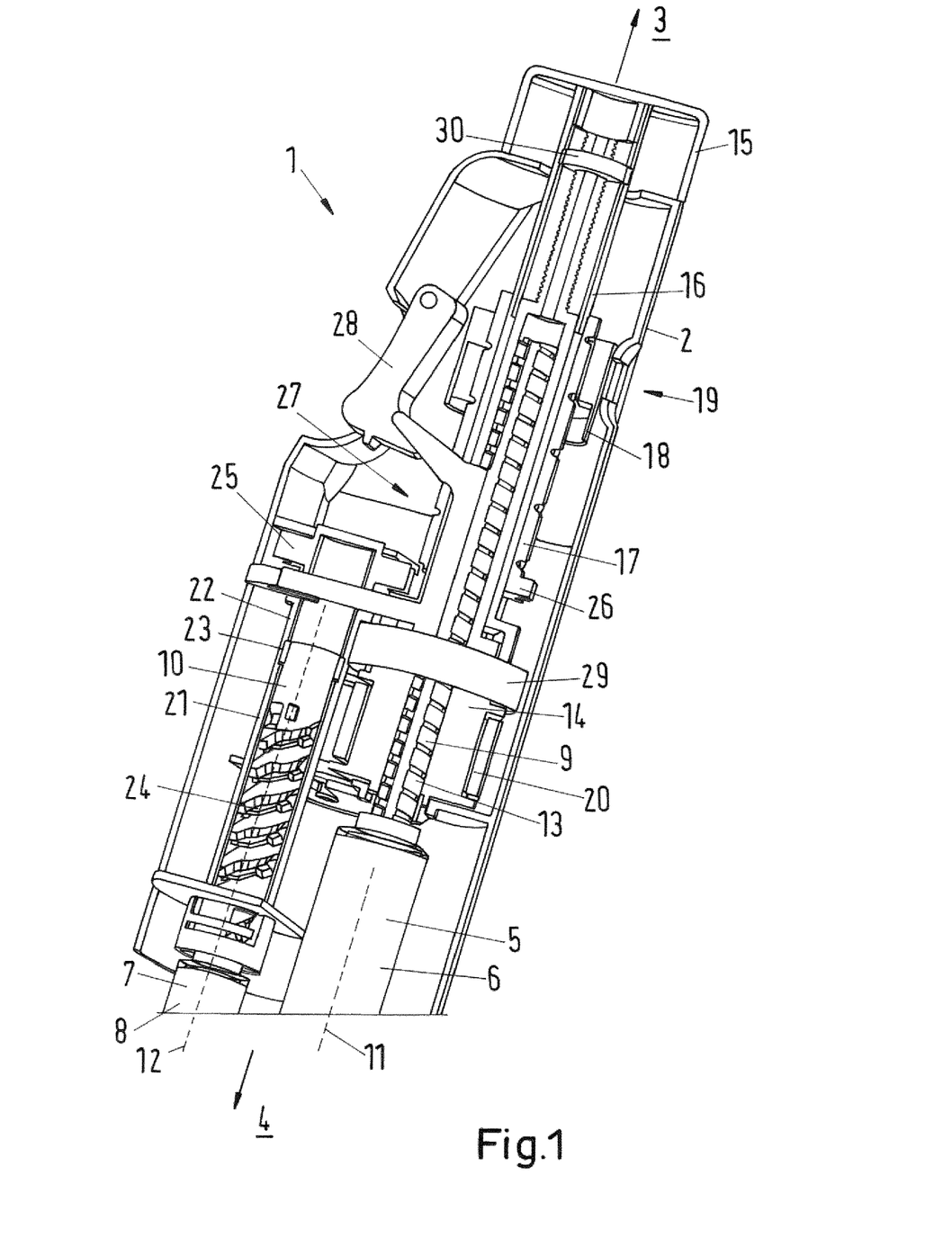
FIG. 1 shows in a perspective sectional cut-view a drug delivery device with a dispense mechanism.

FIG. 1 gives a three-dimensional cut-away view of a drug delivery device 1 configured as a pen-type injector. The drug delivery device 1 comprises a drug delivery device housing assembly 2 which extends from a proximal end 3 to a distal end 4 in axial direction. At the distal end 4, there are two single medicament cartridges accommodated in the housing assembly 2. A primary medicament cartridge 5 is filled with a primary medicament 6, e.g. insulin, and a secondary medicament cartridge 7 contains a secondary medicament 8, e.g. GLP-1.

The dispense mechanism includes a primary lead screw 9 for the dispense of the primary medicament 6 and a secondary lead screw 10 for the dispense of the secondary medicament 8.

The primary lead screw 9 extends along a first longitudinal axis 11, while the secondary lead screw 10 extends along a second longitudinal axis 12. The longitudinal axis 11 of the primary lead screw 9 and the longitudinal axis 12 of the secondary lead screw 10 are arranged in a parallel relationship and extend substantially parallel to the longitudinal axis of the drug delivery device 1. At the respectively distal end of the primary lead screw 9 and at the distal end of the secondary lead screw 10, a bearing is respectively provided, said bearings serve for driving a bung (not shown) in the respective medicament cartridge in distal direction such that the respective medicament is out of the cartridge and dispensed from a needle hub (not shown) that can be attached to the distal end of the drug delivery device 1. Such needle hub comprises a distal injection needle for injecting the medicaments 6, 8 into the patient. Further, the needle hub comprises two proximal needles, each of the needles establishing fluid communication between the common injection needle and the respective medicament 6, 8.

The primary lead screw 9 has a helical thread 13 on its outer surface and is in threaded engagement with a primary drive member 14 which is configured as a primary drive sleeve accommodating partly the primary lead screw 9. Further, the primary lead screw 9 is rotationally keyed to the housing assembly 2 such that when the primary drive sleeve 14 is rotated in one direction (driving direction), the primary lead screw 9 advances in distal direction. At the proximal end 3 of the device 1, a dial grip 15 is rotationally fixed to a dial sleeve 16, the dial sleeve 16 extending in axial direction and partly accommodating a distal end of the primary drive sleeve 14. The dial sleeve 16 extends through a dose dial component 17 configured as a number sleeve. The number sleeve 17 is rotationally keyed to the dial sleeve 16. Further, the number sleeve 17 is threaded to a threaded insert 18 such that the number sleeve 17 moves helically in axial direction relative to the threaded insert 18 and the housing assembly 2 when the number sleeve 17 rotates about the longitudinal axis 11. On the outer peripheral surface of the number sleeve 17, dose numbers are printed on the outer surface of the number sleeve 17 in a helical pattern. A dose of the primary medicament 6 is set by rotating the dial grip 15 wherein this rotation is transferred to the number sleeve 17 which moves in proximal direction. The respective dose number can be captured through a dose window 19.

For rotating the primary drive sleeve 14, a power reservoir in the form of a pre-loaded respectively factory-charged tensator spring 20 is provided, said spring 20 ensuring that the user force and torque required to set and dispense a dose are minimal. The primary drive sleeve 14 is attached to said pre-charged tensator spring 20, which urges the primary drive sleeve 14 in a rotational movement around the longitudinal axis 11. When the primary drive member 4 is allowed to rotate, the primary lead screw 9 is driven in distal direction.

The secondary lead screw 10 is surrounded by a secondary drive member 21 configured as a secondary drive sleeve. The secondary drives sleeve 21 is rotationally keyed to the secondary lead screw 10. For that purpose, the inner surface of the secondary drive sleeve 21 is provided with an axially extending groove 22 engaged by an outer protrusion 23 of the secondary lead screw 10 such that the secondary lead screw 10 can displace in axial direction along the longitudinal axis 12 with respect to the secondary drive sleeve 21 but cannot rotate. The secondary lead screw 9 is provided with an outer helical thread 24 wherein the secondary lead screw 10 is threaded to the housing assembly 2. Consequently, when the secondary drive member 21 rotates along the longitudinal axis 12, this rotation is transferred into the secondary lead screw 10, which moves through the threaded engagement with the housing assembly 2 in distal direction such as to act on the bung in the secondary medicament cartridge 7.

The primary lead screw 9 and the secondary lead screw 10 are part of the dispense mechanism of the drug delivery device. By rotating the dial grip 15, the user can set a desired variable dose of the primary medicament 6. Accordingly, this mechanism can be characterized as a variable dose mechanism. However, the user is not able to set a variable dose of the secondary medicament 9. This is due to the fact that during dispense, when the primary drive member 14 is rotated by the force of the tensator spring 20, the secondary drive sleeve 21 is automatically coupled to the primary drive sleeve 14 such that the dispense mechanism for the secondary lead screw 10 is actuated. The amount of medicament that is dispensed is predetermined and cannot be influenced by the user. Accordingly, this mechanism can be characterized as a fixed dose mechanism.

Figure 2:
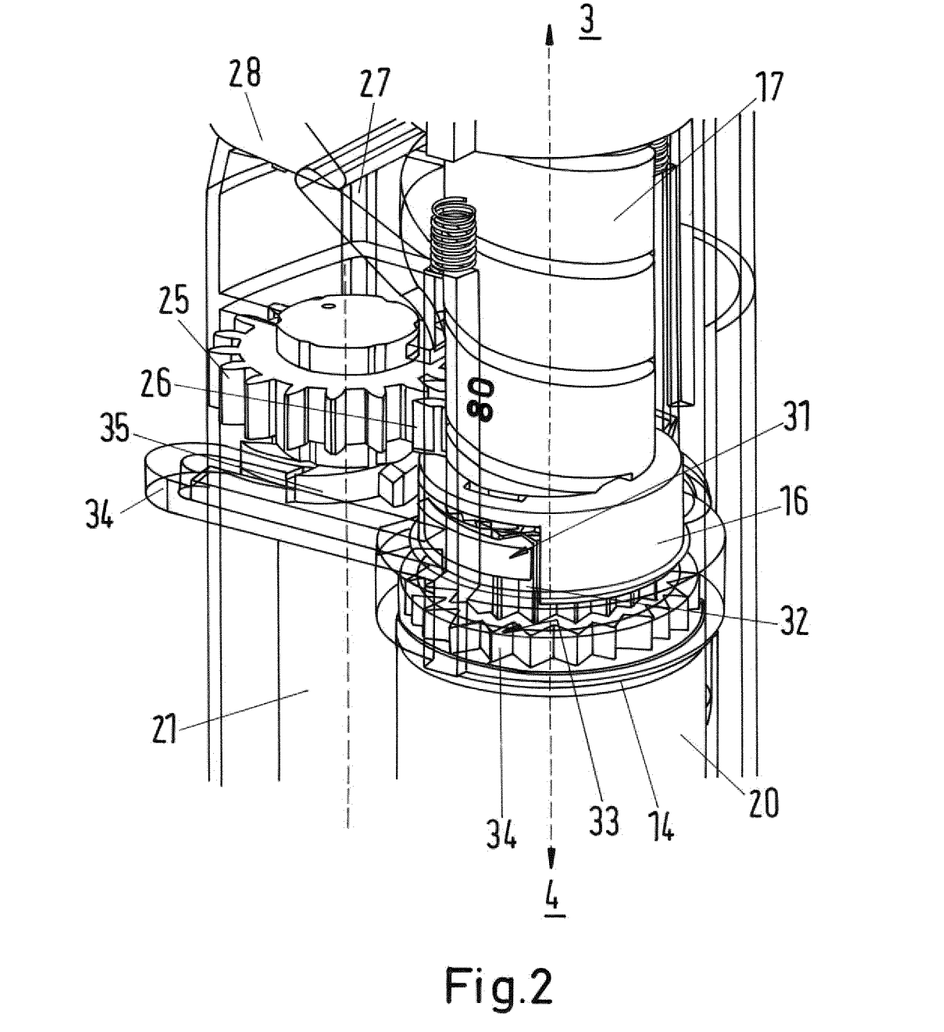
FIG. 2 shows in a perspective cut-view an intermediate section of the drug delivery device.

The secondary drive sleeve 21 is provided with tooth features 25. The number sleeve 17 is provided with corresponding tooth features 26. The tooth features 25, 26 are configured for a mutual meshed engagement such that when the tooth features 25, 26 are engaged, the number sleeve 17 and the secondary drive sleeve 21 are rotationally coupled. The number sleeve 17 serves as a coupling member for rotationally coupling the primary drive member 14 to the secondary drive member 21. During dispense, the number sleeve 17 moves from a proximal first position into a distal second position in which the tooth features 26 of the number sleeve 17 engage the tooth features 25 on the secondary drive sleeve such that the secondary drive member 21 is rotationally coupled to the primary drive sleeve 14 via the number sleeve 17. The movement of the number sleeve 17 from said proximal position into the engagement with the secondary drive member 21 is initiated, respectively controlled by the driving action, respectively the rotation of the primary drive member 14, to drive the primary lead screw 9 in distal direction. To initiate the dispense, a lock mechanism 27 is provided, said lock mechanism including a trigger 28 and a lock element 29. The lock element 29 is formed on the lock mechanism 27, which is substantially constituted by a trigger lock, said trigger lock being axially guided in the housing assembly 2 (not shown).

The trigger 28 is pivotally mounted in the housing assembly 2 such that when the trigger 28 is pressed into the housing 2, the trigger lock 27 is raised axially and moved in proximal direction.

As indicated above, during dose setting the number sleeve 17 is rotationally fixed to the dial sleeve 16 and moves helically relative to the threaded insert 18 and relative to the secondary drive member 21 in proximal direction. When the member sleeve 17 is in the distal (second) position as shown in FIG. 2, the tooth features 25 of the secondary drive sleeve 21 and the tooth feature 26 of the number sleeve 17 engage. During dose setting, the number sleeve 17 moves proximally into a position in which the tooth features 25 and 26 are disengaged. Generally, each proximal position, in which there is no engagement between the number sleeve 17 and the secondary drive member 21 and no rotational movement can be transferred, may be referred to as a first proximal position.

With respect to FIG. 1, at the proximal end of the primary drive sleeve 14, a last dose nut 30 is threaded to the primary drive sleeve 14 and is rotationally keyed to the dial sleeve 16. During dialing, the last dose nut 30 rotates with the dial grip 15 and travels axially on its thread until it reaches a stop position indicating that the variable cartridge 5 has been expanded.

The dial sleeve 16 is provided with a clicker arm 31 (FIG. 2) engaging teeth features 32 on the primary drive sleeve 14, wherein the clicker arm 31 on the dial sleeve 16 is free to click over the teeth features 32 on the primary drive sleeve 14 during dose setting and unsetting to provide the user with tactile feedback and to ensure that discret units of medicament are dialed. As a dose is dialed, the travel of the number sleeve 17 away from the primary drive sleeve 14 in proximal direction controls the dose that is to be delivered. The trigger lock 27 is rotationally keyed to the housing and has a number radially inwardly directed protrusions 33 engaging corresponding features such as recesses 34 (see FIG. 4) on the outer surface of the primary drive sleeve 14. The protrusions 33 engage the recesses 34 when the trigger lock 27 is in the distal position as shown in FIG. 2. When the trigger lock 27 is moved in proximal direction, the trigger lock protrusions 33 disengage from the primary drive sleeve 14 such that the primary drive sleeve 14 is free to rotate under the force of the tensator spring 20. Since the primary drive sleeve is attached to the tensator spring 20, the primary lead screw 9 cannot be advanced and the device 1 cannot dispense the primary medicament 5 when the trigger lock 27 is in the distal position.

A dose of the secondary medicament 8 is automatically set when a variable dose of the primary medicament 5 is set beyond a predefined volume. When the dial grip is rotated, this rotation is transferred to the secondary drive member 21 via the meshed engagement between the tooth features 25, 26 until the number sleeve 17 has been moved in proximal direction and the tooth features 25, 26 disengage. When the user starts to dial a dose, the tooth features 25, 26 act to backwind the secondary drive sleeve 21, which in turn causes the secondary lead screw 10 to rotate and thus travel away from the cartridge bung by a small amount as the backwind rotation of the secondary drive sleeve 21 is opposite the direction the secondary drive sleeve 21 has to be rotated to drive the secondary lead screw 10 in distal direction. The trigger lock 27 is provided with a trigger lock spring arm 35 and the secondary drive member 21 is provided with ratchet features 36 to interlock with said trigger lock spring arm 35. As the secondary drive sleeve 21 is backwound, the spring arm 35 compresses against the ratchet features 36, until the teeth features 25 and 26 of the secondary drive sleeve 21 and the number sleeve 17 disengage during dose setting, which is in the shown embodiment after proximately 47° of rotation of the number sleeve 17. Then, the spring arm 35 rotates the secondary drive sleeve 21 and hence the secondary lead screw back to their original positions.

Thereby, a prime dose of the primary medicament can be dialed and dispensed without effecting the fixed dose mechanism. If a variable dose of the primary medicament 5 is dialed said dose being so small that it does not cause disengagement of the tooth features 25, 26, the subsequent dispense would merely cause to rotate the secondary drive member 21 in the opposite direction such that the secondary lead screw is rotated back to the original position. A dispense of the secondary medicament 8 does not take place. In other words, a dose of the secondary medicament 8 is dispensed when during dose setting, the number sleeve 17 is moved in proximal direction such that the tooth features 25, 26 disengage, so that the spring arm 35 resets the secondary drive sleeve 21 so that during dose dispense, when the tooth features 25, 25 reengage, the secondary lead screw 10 is moved in distal direction from the starting position.

To deliver a dose, the trigger 28 is pressed so that the trigger lock 27 is raised axially. This axial travel disconnects the protrusions respectively teeth features 33, 34 of the trigger lock 27 from the primary drive sleeve 14 so that the primary drive sleeve is free to rotate under the applied torque of the tensator spring 20. This rotation causes the primary medicament 5 to be delivered. Simultaneously, while the trigger lock 27 is in the proximal position, it moves over the dial sleeve clicker arm 31 such that the dial sleeve clicker arm 31 cannot move in radially outward direction, thereby locking the dial grip 15 to the primary drive sleeve 14. When the user holds the dial grip 15 during dose delivery, the mechanism will stop, which ensures that the number sleeve 17 always displays the correct dose. While in the proximal position, the trigger lock spring arm 35 is also lifted clear of the secondary drive sleeve ratchet features 36.

Figure 3:
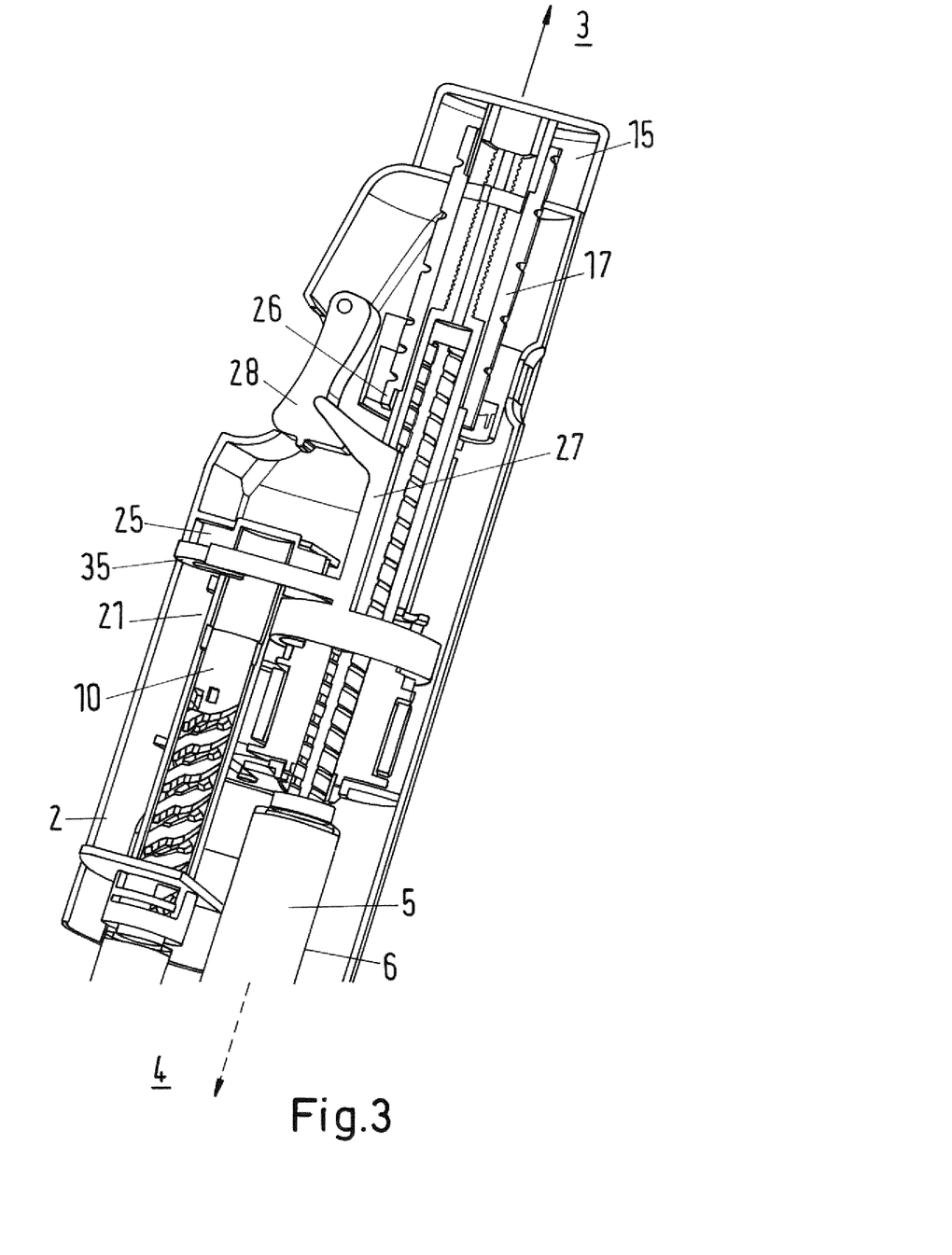
FIG. 3 shows in a cut-view a proximal section of the drug delivery device.

FIG. 3 shows the drug delivery device 1 after dose setting by rotating the dial grip 15. The number sleeve 17 has traveled in proximal direction during dose setting such that the tooth features 25 of the secondary drive sleeve 21 and the tooth features 26 of the number sleeve 17 have disengaged and the trigger lock spring arm 35 has reset the secondary drive sleeve 21. During dose delivery, by pressing against the trigger 28, the number sleeve 17 travels helically in distal direction under the rotational force of the tensator spring towards the primary medicament cartridge 7. Near the end of the dispense, the tooth features 26 on the number sleeve 17 reengage with the tooth features 25 of the secondary drive sleeve 21. This causes the secondary drive sleeve 21 to rotate. The rotation of the secondary drive sleeve 21 causes rotation of the secondary lead screw 10 which is converted into axial movement in distal direction via the threaded connection with the housing assembly 2 such that a predetermined and non-user adjustable dose of the secondary medicament is dispensed.

While the trigger lock 27 is in the proximal position, the trigger lock spring arm 35 is also lifted clear of the ratchet features of the secondary drive sleeve 21. This allows the secondary drive sleeve 21 to rotate when acted upon the other gear tooth features 26 of the number sleeve 17 as the number sleeve 17 returns from the proximal position in distal direction, respectively from a first proximal position into the second distal position such that the tooth features 25, 26 reengage and rotation of the number sleeve 17, which is rotationally locked to the primary drive sleeve 14 during dose dispense, is transferred to the secondary drive member 21.

Figure 4:
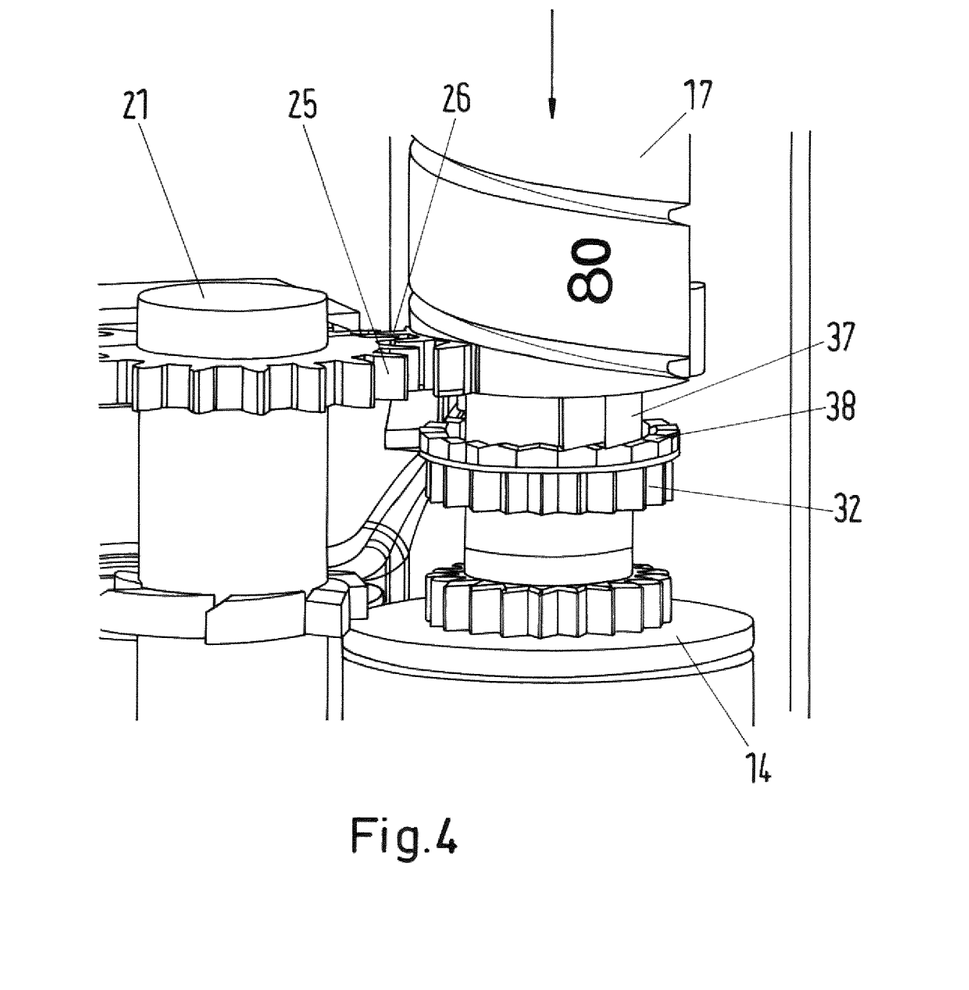
FIG. 4 shows in a side view the engagement between the primary drive member, the secondary drive member and the coupling member.

As shown in FIG. 4, during dose delivery, the number sleeve 17 travels helically in distal direction as indicated by the arrow. Near the end of the dispense the tooth features 25, 26 reengage. When the number sleeve 17 returns to the zero units position, it hits a stop feature and cannot rotate further such that further rotation of the primary drive sleeve 14 is prevented and only the set dose is delivered. Said stop feature may be provided in the thread engagement between the number sleeve 17 and the threaded insert and can be constituted by an end of the thread. Furthermore, said stop feature may be provided in an engagement in the primary drive sleeve 14 and the number sleeve 17. As obvious from FIG. 4, the number sleeve 17 has at its distal end stop faces 37 engaging corresponding faces formed like teeth 38 on the primary drive sleeve 14. In the zero unit position as shown in FIG. 4, the primary drive sleeve 14 is held against said stop faces 37 of the number sleeve 17. In this position, the number sleeve 17 cannot travel in distal direction.

When a dose is dialed, the primary drive sleeve 14 is held against the ratchet engagement of the clicker arm 31 of the dial sleeve 16. There has to be some clearance between these features so that they can engage correctly when required. This means that when a dose is dialed, the primary drive sleeve 14 can rotate slightly. To prevent this rotation causing the primary lead screw to advance, the zero unit stop faces 37, 38 between the number sleeve 17 and the primary drive sleeve 14 are helical and have the same pitch as the primary lead screw thread. Further, there is some axial float in the primary drive sleeve 14 so that when the stop faces 37, 38 contact each other, any rotation of the primary drive sleeve 14 results in some additional axial movement so that the component follows the same helical path as the primary lead screw thread 13. This means that the primary drive sleeve moves over the primary lead screw without causing it to advance.

Figure 5:
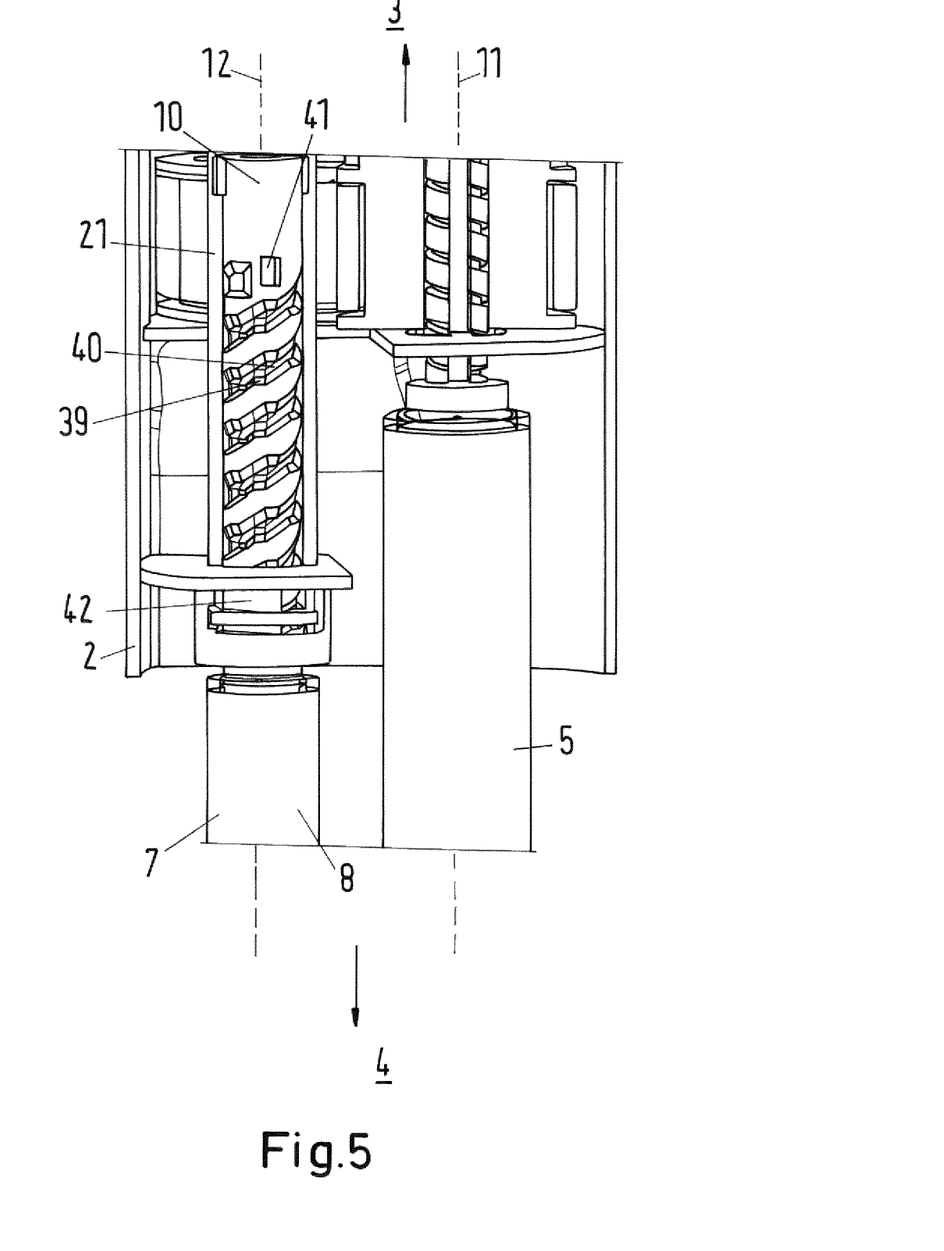
FIG. 5 shows in a cut-view a distal section of the drug delivery device.

As shown in FIG. 5, the outer thread of the secondary lead screw 10 comprises helical segments 39 and non-helical segments 40 alternately arranged in a helical pattern. Due to the structure, when the secondary lead screw 10 rotates in the threaded engagement of the housing assembly 2 during a first phase of the dispensing rotation of the secondary lead screw, the secondary lead screw 10 advances in distal direction. Toward the end of the dose, in a second phase of the dispensing, with typically one unit of variable dose medicament remaining to be in dispense, the secondary lead screw 10 rotates on the flat respectively non-helical portions 40 such that the secondary lead screw 10 does not advance in distal direction 4, while the secondary drive sleeve 21 rotates. A secondary medicament is not dispensed during this phase of the dispensing. Instead, an injection needle receives only primary medicament 5 which acts to purge the secondary medicament 8 from the needle hub assembly. This ensures that the user receives the correct dose.

At the proximal end of the secondary lead screw 10, a last dose stop feature 41 is provided. At the end of life of the secondary medicament cartridge 7, the secondary lead screw 10 is locked against further rotation by the last dose stop feature 41 of the secondary lead screw 10 engaging a corresponding stop feature 42 of the housing assembly 2. This feature acts as a ratchet arm that engages the stop feature 41 on the secondary lead screw 10 which is configured as a slot so that after all doses have been delivered from the second medicament cartridge, the ratchet arm 42 engages the slot and prevents further setting of the device.

REFERENCE NUMERALS 1 drug delivery device
2 housing assembly
3 proximal end
4 distal end
5 primary medicament cartridge
6 primary medicament
7 secondary medicament cartridge
8 secondary medicament
9 primary lead screw
10 secondary lead screw
11 longitudinal axis of primary lead screw
12 longitudinal axis of secondary lead screw
13 helical thread on primary lead screw
14 primary drive sleeve (primary drive member)
15 dial grip
16 dial sleeve
17 number sleeve (coupling member)
18 threaded insert
19 dose window
20 tensator spring (power reservoir)
21 secondary drive sleeve (secondary drive member)
22 axial extending groove
23 projection
24 outer thread of secondary lead screw
25 tooth features on secondary drive sleeve
26 tooth features on number sleeve
27 lock mechanism/trigger lock
28 trigger
29 lock element
30 last dose nut
31 clicker arm
32 teeth features on primary drive sleeve
33 trigger lock protrusion
34 recesses
35 trigger lock spring arm
36 ratchet features
37 stop faces/teeth
38 stop faces/teeth
39 helical segment
40 non-helical segment
41 last dose stop feature
42 stop feature

The invention claimed is:

1. A dispense mechanism for a drug delivery device, the dispense mechanism comprising:
    a primary drive member for driving a primary lead screw;
    a secondary drive member for driving a secondary lead screw, the primary drive member and the secondary drive member being configured to rotate during dose dispense;
    a power reservoir for rotating the primary drive member;
    a lock element configured to prevent the primary drive member from driving the primary lead screw;
    an actuateable release mechanism configured to disengage the lock element from the primary drive member such that the primary drive member is free to rotate under the force of the power reservoir; and
    a coupling member for rotationally coupling the primary drive member to the secondary drive member and configured to move during the dose dispense from a first position in which the primary drive member is rotationally decoupled from the secondary drive member into a second position in which the primary drive member is rotationally coupled to the secondary drive member, the coupling member being rotationally coupled to the primary drive member during dose dispense and being threaded to the housing assembly or a housing component such that rotation of the primary drive member moves the coupling member from the first position into the second position, such that rotation of the primary drive member is transferred to the secondary drive member.

2. The dispense mechanism according to claim 1, wherein the coupling member is configured to be rotationally coupled to the primary drive member during dose dispense.

3. The dispense mechanism according to claim 1, wherein the secondary drive member and the coupling member are configured for meshed engagement.

4. The dispense mechanism according to claim 1, wherein the secondary lead screw is configured such that, when the secondary drive member is rotated, the secondary lead screw advances in distal direction relative to the secondary drive member during a first phase, and such that the secondary lead screw remains stationary in axial direction relative to the rotating secondary drive member during a second phase.

5. The dispense mechanism according to claim 1, wherein the secondary lead screw comprises a thread, and the thread comprises helical segments and non-helical segments.

6. The dispense mechanism according to claim 1, wherein the secondary lead screw is in threaded engagement with a housing assembly.

7. The dispense mechanism according to claim 1, further comprising a user actuateable dial grip and a lock mechanism, and the lock mechanism is configured to rotationally lock the dial grip to the primary drive member during dose dispense.

8. The dispense mechanism according to claim 1, wherein the coupling member comprises a stop feature for locking the primary drive member against rotation after a set dose of a primary medicament is dispensed.

9. The dispense mechanism according to claim 1, wherein the coupling member is rigidly connected to a dose dial component in threaded engagement with a housing assembly.

10. The dispense mechanism according to claim 1, further comprising a biasing member configured to urge the secondary drive member in a rotational direction opposite a driving direction.

11. The dispense mechanism according to claim 10, wherein the biasing member is configured to disengage from the secondary drive member during dispense.

12. The dispense mechanism according to claim 11, wherein the biasing member is axially movable relative to the secondary drive member.

13. A drug delivery device comprising:
a primary drug delivery assembly for delivery of a primary medicament contained in a primary cartridge;
a secondary drug delivery assembly for delivery of a secondary medicament contained in a secondary cartridge; and
a dispense mechanism comprising:
a primary drive member for driving a primary lead screw;
a secondary drive member for driving a secondary lead screw, the primary drive member and the secondary drive member being configured to rotate during dose dispense;
a power reservoir for rotating the primary drive member;
a lock element configured to prevent the primary drive member from driving the primary lead screw;
an actuatable release mechanism configured to disengage the lock element from the primary drive member such that the primary drive member is free to rotate under the force of the power reservoir; and
a coupling member for rotationally coupling the primary drive member to the secondary drive member and configured to move during the dose dispense from a first position in which the primary drive member is rotationally decoupled from the secondary drive member into a second position in which the primary drive member is rotationally coupled to the secondary drive member, the coupling member being rotationally coupled to the primary drive member during dose dispense and being threaded to the housing assembly or a housing component such that rotation of the primary drive member moves the coupling member from the first position into the second position, such that rotation of the primary drive member is transferred to the secondary drive member.

14. The drug delivery device of claim 13, further comprising the primary cartridge containing the primary medicament, the primary medicament including at least one human insulin or a human insulin analogue or derivative.

15. The drug delivery device of claim 13, further comprising the secondary cartridge containing the secondary medicament, the secondary medicament including a glucagon-like peptide or a glucagon analogue or derivative.

16. A method of dispensing a medicament using a dispense mechanism, the dispense mechanism comprising:
a primary drive member for driving a primary lead screw;
a secondary drive member for driving a secondary lead screw, the primary drive member and the secondary drive member being configured to rotate during dose dispense;
a power reservoir for rotating the primary drive member;
a lock element configured to prevent the primary drive member from driving the primary lead screw;
an actuateable release mechanism configured to disengage the lock element from the primary drive member such that the primary drive member is free to rotate under the force of the power reservoir; and
a coupling member for rotationally coupling the primary drive member to the secondary drive member and configured to move during the dose dispense from a first position in which the primary drive member is rotationally decoupled from the secondary drive member into a second position in which the primary drive member is rotationally coupled to the secondary drive member, the coupling member being rotationally coupled to the primary drive member during dose dispense and being threaded to the housing assembly or a housing component such that rotation of the primary drive member moves the coupling member from the first position into the second position, such that rotation of the primary drive member is transferred to the secondary drive member;
the method comprising:
dispensing, by driving the primary lead screw with the primary drive member, a dose of a primary medicament from a primary cartridge during a first phase, the dose of the primary medicament being adjustable; and
dispensing, by driving the secondary lead screw with the secondary drive member, a dose of a secondary medicament from a secondary cartridge during a second phase after the first phase, the dose of the secondary medicament being fixed.

17. The method according to claim 16, wherein the dispensing of the dose of the primary medicament is initiated when a user operates a user the actuateable release mechanism, and the dispensing of the dose of the secondary medicament is automatically initiated when a remainder of the dose of the primary medicament reaches a predefined threshold amount.

18. The method according to claim 16, wherein the dose of the primary medicament and the dose of the secondary medicament are dispensed through a single injection needle.

* * * * *